(12) United States Patent
Evans

(10) Patent No.: US 10,085,697 B1
(45) Date of Patent: Oct. 2, 2018

(54) PULSE OXIMETER SYSTEM

(71) Applicant: Mollie Evans, Omaha, NE (US)

(72) Inventor: Mollie Evans, Omaha, NE (US)

( * ) Notice: Subject to any disclaimer, the term of this patent is extended or adjusted under 35 U.S.C. 154(b) by 1297 days.

(21) Appl. No.: 13/964,842

(22) Filed: Aug. 12, 2013

Related U.S. Application Data

(60) Provisional application No. 61/681,683, filed on Aug. 10, 2012.

(51) Int. Cl.
*A61B 5/00* (2006.01)
*A61B 5/11* (2006.01)
*A61B 5/1455* (2006.01)

(52) U.S. Cl.
CPC .......... *A61B 5/746* (2013.01); *A61B 5/0002* (2013.01); *A61B 5/11* (2013.01); *A61B 5/14551* (2013.01)

(58) Field of Classification Search
CPC ......... A61B 5/746; A61B 5/0002; A61B 5/11; A61B 5/14551
USPC ....................................... 600/301
See application file for complete search history.

(56) References Cited

U.S. PATENT DOCUMENTS

| | | |
|---|---|---|
| 5,505,199 A | 4/1996 | Kim |
| 5,515,865 A | 5/1996 | Scanlon |
| 5,830,137 A | 11/1998 | Scharf |
| 5,842,982 A | 12/1998 | Mannheimer |
| 6,047,201 A * | 4/2000 | Jackson, III ......... A61B 5/0002 128/903 |
| 6,208,897 B1 | 3/2001 | Jorgenson et al. |
| 6,289,238 B1 | 9/2001 | Besson et al. |
| 6,492,634 B2 | 12/2002 | Marchitto et al. |
| 6,498,652 B1 | 12/2002 | Varshneya et al. |
| 6,553,242 B1 | 4/2003 | Sarussi |
| 6,553,256 B1 | 4/2003 | Jorgenson et al. |
| 6,879,850 B2 | 4/2005 | Kimball |
| 7,006,855 B1 | 2/2006 | Sarussi |
| 7,035,432 B2 | 4/2006 | Szuba |
| 7,171,251 B2 | 1/2007 | Sarussi et al. |
| 7,215,991 B2 | 5/2007 | Besson et al. |
| 7,359,741 B2 | 4/2008 | Sarussi |
| 7,590,438 B2 | 9/2009 | Sarussi et al. |
| 7,603,152 B2 | 10/2009 | Sarussi et al. |
| 7,606,607 B2 | 10/2009 | Sarussi et al. |
| 7,613,490 B2 | 11/2009 | Sarussi et al. |
| 7,650,176 B2 | 1/2010 | Sarussi et al. |

(Continued)

FOREIGN PATENT DOCUMENTS

| | | |
|---|---|---|
| CA | 2334964 A1 | 12/1999 |
| CN | 101108125 A | 1/2008 |

(Continued)

*Primary Examiner* — Gary Jackson
*Assistant Examiner* — Sebastian X Lukjan
(74) *Attorney, Agent, or Firm* — Ryan T. Grace; Advent, LLP.

(57) ABSTRACT

Pulse oximeter systems are described that detect an oxygen level of a user and/or monitor a user's heart rate. The pulse oximeter systems are configured to provide an alert when a user's detected oxygen level decreases below an established oxygen level, and/or when a user's heart rate decreases below a lower threshold value and/or increases above an upper threshold value. For example, an alert may be provided when a user's detected oxygen level decreases by more than about five percent (5%) of an established oxygen level. In some instances, an operator can set a level at which an alert will be provided.

13 Claims, 3 Drawing Sheets

(56) References Cited

U.S. PATENT DOCUMENTS

| | | |
|---|---|---|
| 9,693,730 B2 | 7/2017 | Workman et al. |
| 2002/0013538 A1 | 1/2002 | Teller |
| 2002/0133067 A1 | 9/2002 | Jackson, III |
| 2003/0229276 A1 | 12/2003 | Sarussi et al. |
| 2004/0034293 A1 | 2/2004 | Kimball |
| 2004/0249299 A1 | 12/2004 | Cobb |
| 2005/0113655 A1 | 5/2005 | Hull |
| 2006/0079792 A1* | 4/2006 | Finburgh .............. A61B 5/022 600/485 |
| 2007/0073119 A1 | 3/2007 | Wobermin et al. |
| 2007/0273504 A1* | 11/2007 | Tran ................... A61B 5/0022 340/539.12 |
| 2009/0112769 A1 | 4/2009 | Dicks et al. |
| 2009/0216556 A1 | 8/2009 | Martin et al. |
| 2009/0247849 A1 | 10/2009 | McCutcheon et al. |
| 2010/0081901 A1 | 4/2010 | Buice et al. |
| 2011/0288379 A1 | 11/2011 | Wu |
| 2012/0083670 A1* | 4/2012 | Rotondo .............. A61B 5/1116 600/301 |
| 2012/0157757 A1 | 6/2012 | Eyck et al. |
| 2012/0179479 A1 | 7/2012 | Waterson et al. |
| 2012/0245447 A1 | 9/2012 | Karan et al. |
| 2013/0137938 A1* | 5/2013 | Peters ................. A61B 5/0205 600/301 |
| 2013/0261415 A1 | 10/2013 | Ashe et al. |

FOREIGN PATENT DOCUMENTS

| | | |
|---|---|---|
| EP | 1139865 A1 | 10/2001 |
| IL | 121079 | 6/1997 |
| JP | 2008194323 A | 8/2008 |
| WO | 2012025829 A2 | 3/2012 |
| WO | 2012082297 A2 | 6/2012 |

* cited by examiner

PULSE OXIMETER SYSTEM

CROSS-REFERENCE TO RELATED APPLICATIONS

The present application claims the benefit under 35 U.S.C. § 119(e) of U.S. Provisional Application Ser. No. 61/681,683, filed Aug. 10, 2012, and titled "PULSE OXIMETER SYSTEM," which is herein incorporated by reference in its entirety.

BACKGROUND

Pulse oximetry generally refers to non-invasive techniques for monitoring the oxygenation of hemoglobin in an individual's body, such as a human body. Pulse oximeters are typically used when an individual's oxygenation may be unstable. For example, pulse oximeters can be used in intensive care settings, emergency room settings, operating room settings, recovery room settings, and for pilots who operate unpressurized aircraft. Pulse oximeters can also be used for mountain climbing, and by athletes whose oxygen levels can decrease at high altitudes or with exercise.

SUMMARY

Pulse oximeter systems are described that detect an oxygen level of a user and/or monitor a user's heart rate. The pulse oximeter systems are configured to provide an alert when a user's detected oxygen level decreases below an established oxygen level, and/or when a user's heart rate decreases below a lower threshold value and/or increases above an upper threshold value. For example, an alert may be provided when a user's detected oxygen level decreases by more than about five percent (5%) of an established oxygen level. In some instances, an operator can set a level at which an alert will be provided.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

In some instances, an infant may experience a lack of oxygen and excessive carbon dioxide levels (e.g., when the infant has a respiratory infection that hampers breathing, or rebreathes exhaled air trapped in underlying bedding when the infant sleeps on the stomach). Typically, an infant can sense inadequate air intake, and the brain triggers the infant to wake from sleep and cry, changes heartbeat and/or breathing patterns to compensate for insufficient oxygen and excess carbon dioxide, and so forth. However, in some instances, an infant may not adequately respond to a lack of oxygen and excessive carbon dioxide. In this type of instance, intervention from a caregiver, such as a parent or guardian, may be desirable.

Accordingly, pulse oximeter systems are described that detect oxygen levels and/or heart rate of a user, such as, but not necessarily limited to, an infant. The pulse oximeter systems are configured to provide an alert when a user's detected oxygen level decreases below an established oxygen level, and/or when a user's heart rate decreases below a lower threshold value and/or increases above an upper threshold value. For example, an alert may be provided when an infant's detected oxygen level decreases by more than about five percent (5%) of an established oxygen level. In some instances, an operator, such as a caregiver, can set a level at which an alert will be provided.

Figures 1A, 1B:
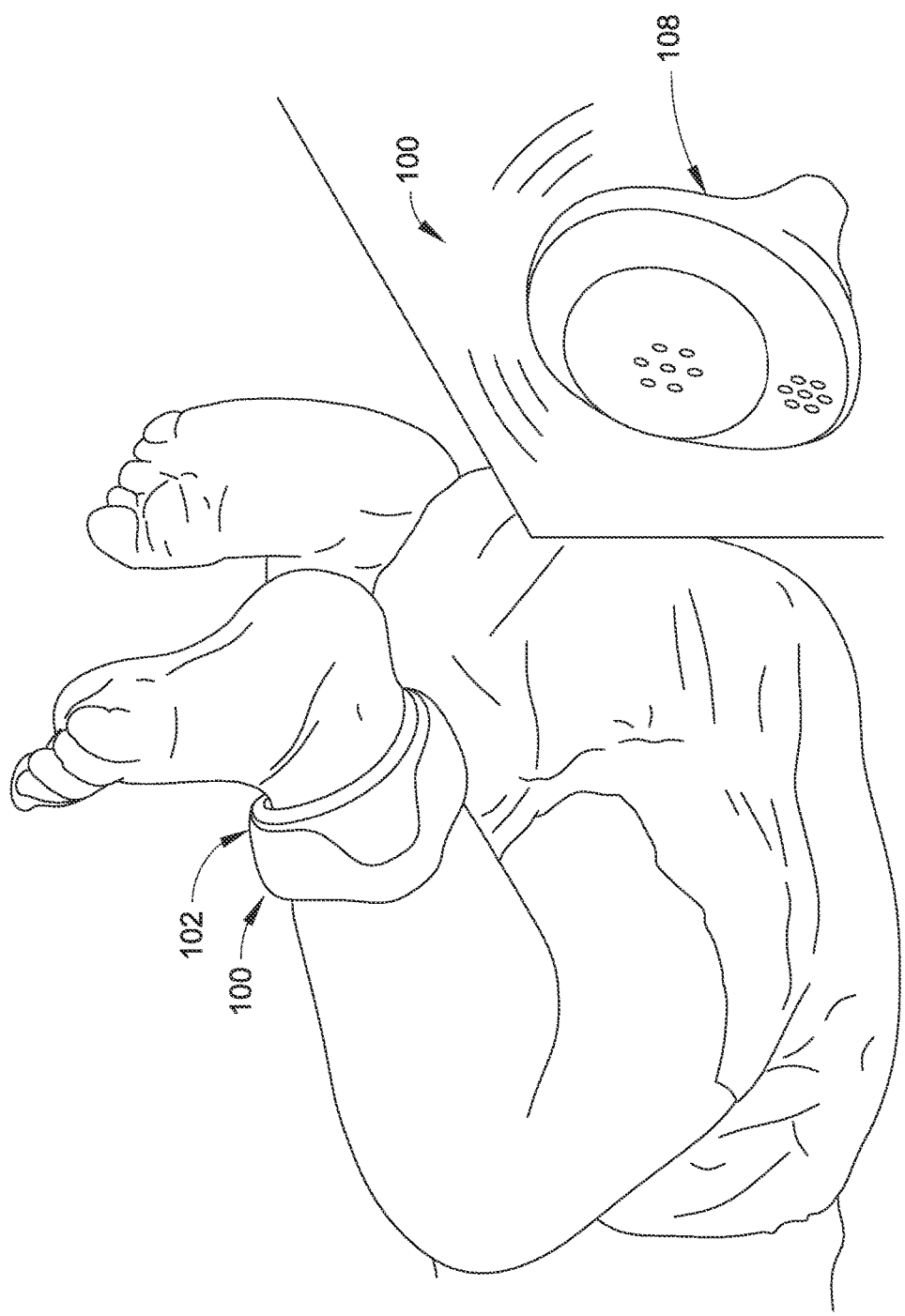
FIG. 1A is a perspective view illustrating a wearable device of a pulse oximeter system, where the wearable device is configured to be worn around the ankle of an infant in accordance with example implementations of the present disclosure.
FIG. 1B is a perspective view illustrating a monitor device of a pulse oximeter system, where the monitor device is positioned in a remote location with respect to a wearable device and configured to communicate with the wearable device in accordance with example implementations of the present disclosure.
Figure 2:
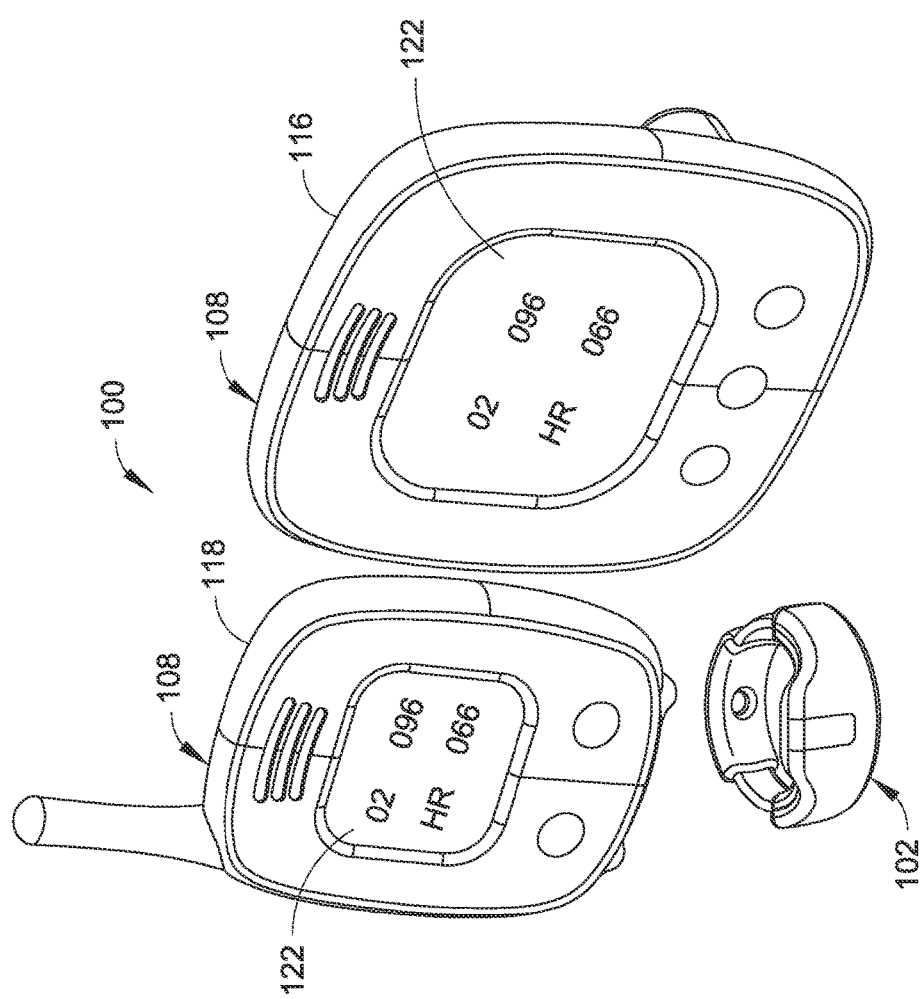
FIG. 2 is a perspective view illustrating of a pulse oximeter system that includes a wearable device, a base station monitor device that communicates with the wearable device, and a handheld monitor device that communicates with the base station monitor device and/or the wearable device in accordance with example implementations of the present disclosure.
Figure 3:
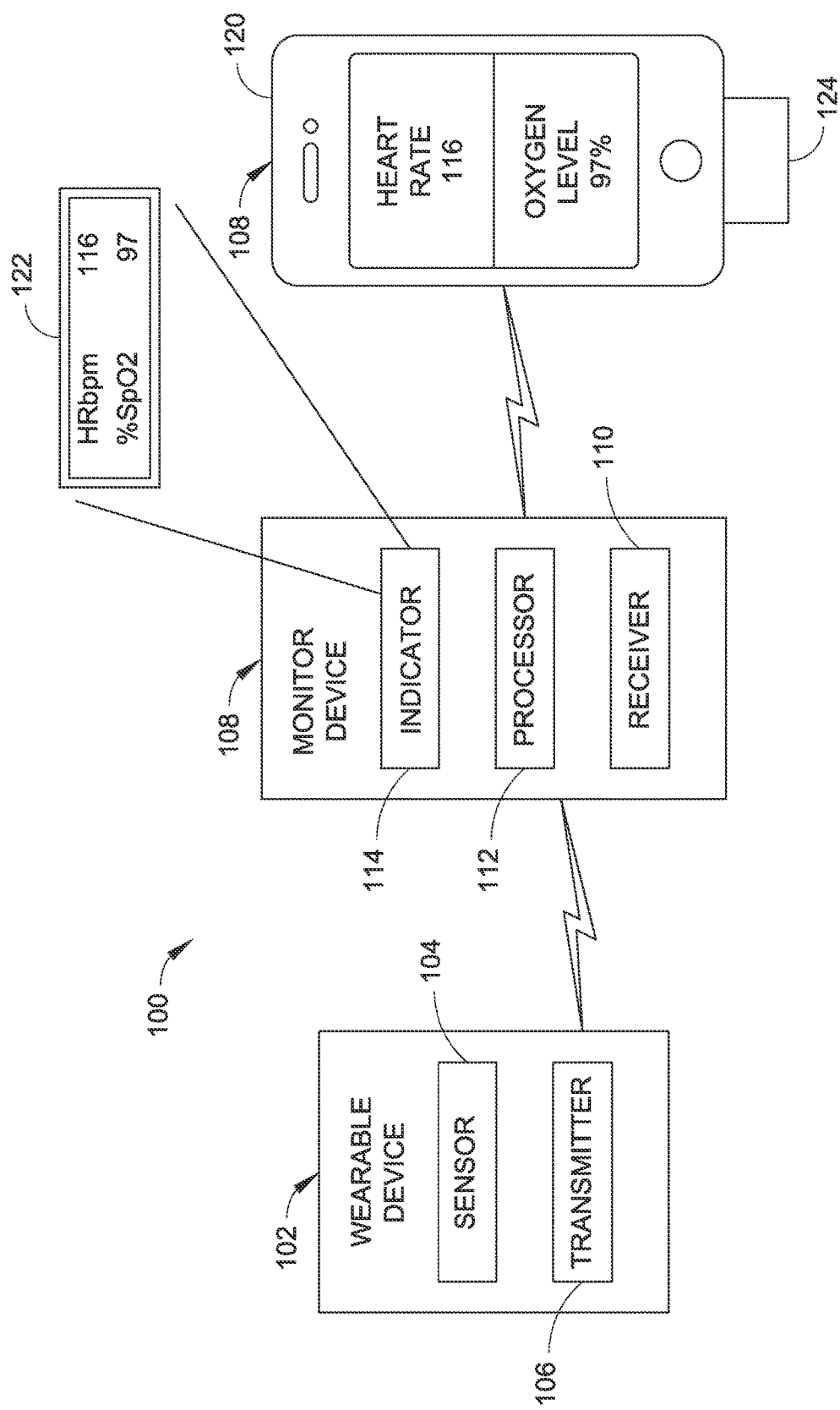
FIG. 3 is a diagrammatic illustration of a pulse oximeter system that includes a wearable device, a monitor device that communicates with the wearable device, and a smart phone that communicates with the monitor device in accordance with example implementations of the present disclosure.

FIGS. 1 through 3 illustrate example systems 100 configured to detect (e.g., measure) oxygen levels and/or heart rate of a user and provide an alert when a user's detected oxygen level decreases below an established oxygen level, and/or when a user's heart rate decreases below a lower threshold value and/or increases above an upper threshold value. The pulse oximeter systems 100 include a first device 102 (e.g., a bracelet) configured to be wearable by a user. The wearable device 102 includes a sensor 104 (e.g., a pulse oximeter) for detecting an oxygen level and/or a heart rate of the user, and a transmitter 106 (e.g., a radio frequency (RF) transmitter) coupled with the sensor 104 for transmitting the detected oxygen level and/or the heart rate of the user to a second device 108 (e.g., to a remote monitor). An example monitor device 108 includes a receiver 110 (e.g., an RF receiver) for receiving the detected oxygen level and/or the detected heart rate of the user from the wearable device 102. The monitor device 108 also includes a processor 112 for comparing the detected oxygen level of the user to an established oxygen level and/or comparing the detected heart rate of the user to an established heart rate, and an identifier (e.g., indicator 114) for providing an alert when the detected oxygen level of the user is less than the established oxygen level, and/or when the detected heart rate of the user decreases below a lower threshold value and/or increases above an upper threshold value. The monitor device 108 can be configured as a base station monitor 116, a handheld monitor 118, or another type of monitor, such as a smart phone 120, or the like.

In implementations, an alert can be provided when a user's detected oxygen level decreases by more than a percentage (e.g., about five percent (5%)) of an established oxygen level. In some instances, an operator can set a level (e.g., a percentage of an established oxygen level) at which an alert will be provided. However, an alert generated when a detected oxygen level decreases by more than a percentage of an established oxygen level is provided by way of example only and is not meant to be restrictive of the present disclosure. Thus, an alert may be provided when one or more other parameters detectable by the sensor 104 correspond to a level less than, equal to, and/or greater than a predetermined threshold level. For instance, an indicator 114 can be used to provide an alert when a user's heart rate decreases below a lower threshold value and/or increases above an upper threshold value.

Two or more different types of parameters can be detected and used together to provide an alert. For instance, an alert can be provided immediately, or at least substantially immediately, when a user's detected oxygen level decreases relative to an established oxygen level and the user's detected heart rate also decreases below a lower threshold value and/or increases above an upper threshold value simultaneously, or at least substantially simultaneously (e.g., to differentiate an anomalous detected oxygen level that may be due to motion of the user from a detected oxygen level that may be due to an actual decrease in the user's oxygen). Further, in an instance where a user's detected heart rate is substantially constant for a period of time, an alert can be provided after the user's detected oxygen level has decreased relative to an established oxygen level and remained below this threshold for the time period. In implementations, a time period can be preprogrammed, selected by an operator (e.g., a caregiver), and so forth.

In some instances, parameters detected and associated with internal bodily functions of a user (e.g., oxygen level, heart rate, and so on) can be used in combination with one or more external parameters that can be detected for the user and/or for a surrounding environment. For example, an alert can be provided immediately, or at least substantially immediately, when a user's detected heart rate increases above an upper threshold value while the user's detected motion remains substantially constant (e.g., to differentiate a detected heart rate that may be due to motion of the user from a detected heart rate that may be due to another condition). Further, in an instance where motion of the user is detected, an alert can be provided after a user's detected heart rate has exceeded an upper threshold value for a period of time, and/or when the user's motion has subsided while the detected heart rate remains elevated. In this configuration, the wearable device 102 can include a sensor for detecting motion, such as an accelerometer for detecting acceleration and/or deceleration. However, detecting a user's motion is provided by way of example only and is not meant to be restrictive of the present disclosure. Thus, other external parameters can also be detected, including, but not necessarily limited to: room temperature, light, noise, vibration, and so forth.

In some instances, an alert can be provided when the receiver 110 stops receiving information from the wearable device 102. For example, the transmitter 106 coupled with the sensor 104 may be moved out of range of the receiver 110. An alert can be provided immediately and/or after a time period (e.g., to differentiate a momentary communications interruption from a loss of communications). In some embodiments, the alert is provided by, for example, a display 122. An alert includes, but is not necessarily limited to: an audible alarm; a visual alarm, such as a flashing indicator light, a flashing display readout, an indicator light having an increased brightness, intensity, luminosity, and so forth; a haptic feedback alarm, such as a vibrating alarm; an electronic message, such as a text message, an email, and so forth; as well as various combinations thereof.

In implementations, the pulse oximeter may be configured to be placed on a thin part of a user's body, such as a fingertip, an earlobe, and/or an ankle or foot (e.g., in the case of an infant). The pulse oximeter may pass light of two or more different wavelengths through the user's body to a photodetector. Using the photodetector, the changing absorbance at each of the various wavelengths can be measured. Based upon this detection, absorbencies due to the pulsing of arterial blood can be determined (e.g., to the exclusion of venous blood, skin, bone, muscle, fat, and so forth). In some instances, near-infrared spectroscopy (NIRS) can be used to detect both oxygenated and deoxygenated hemoglobin on a peripheral scale. However, the pulse oximeter is provided by way of example only and is not meant to be restrictive of the present disclosure. Thus, in other implementations, a variety of sensors can be used with the described techniques, approaches, and/or structures of the present disclosure. For example, a sensor configured for reflectance pulse oximetry may be used. In this configuration, the sensor may be placed on other various parts of a user's body.

In some embodiments, the wearable device 102 and/or the monitor device 108 are configured to communicatively couple with another device configured to detect various characteristic data associated with the user. For example, in some embodiments, the monitor device 108 is wirelessly connected to another sensor device housed in a chest pocket of an article of clothing worn by an infant. The additional sensor device can be configured to detect (e.g., measure) characteristic data, including but not necessarily limited to: body temperature, position, chest movement, and so forth. The detected data is wirelessly transmitted (e.g., continuously, periodically, and so on) to the monitor device 108. In other embodiments, the additional sensor device can be coupled (e.g., via a wired and/or wireless connection) to the wearable device 102. In this configuration, the wearable device 102 collects characteristic data associated with the user and transmits the information to the monitor device 108. In still further embodiments, the additional sensor device transmits characteristic data to both the wearable device 102 and the monitor device 108.

In some instances, parameters detected and associated with internal bodily functions of a user (e.g., oxygen level, heart rate, and so on) are used in combination with characteristic data collected by an additional sensor device. For example, an alert can be provided when a user's detected heart rate increases above an upper threshold value while the user's temperature remains substantially constant (e.g., to differentiate a detected heart rate that may be due to motion of the user from a detected heart rate that may be due to another condition). Further, in an instance where an elevated body temperature is detected, an alert can be provided after a user's detected heart rate has exceeded an upper threshold value for a period of time, and/or when the user's motion has subsided while the body temperature remains elevated.

In some embodiments, one or more additional sensor devices communicatively coupled with the wearable device 102 and/or the monitor device 108 include functionality for capturing audio and/or video of the user. For example, an additional sensor device comprises a high definition (HD) video camera coupled with the monitor device 108. The video camera can be used to observe and/or monitor characteristic information about the user, such as chest compressions. In some instances, the video camera can also be used to monitor oxygen intake, heart rate, and so forth. However, a video camera is provided by way of example only and is not meant to limit the present disclosure. In other embodiments, an additional sensor device comprises a sensor placed on the user's person that is configured to sense movement that can be associated with heart rate and/or oxygen levels. In some instances, an algorithm is used to determine such characteristic information about the user (e.g., by monitoring a characteristic rate of chest compressions identified using HD video, a motion sensor, and so forth). Further, information captured by an additional sensor device can be wirelessly transmitted (e.g., continuously, periodically, and so on) to the monitor device 108 (e.g., where the monitor device 108 comprises a handheld computing device, a smart phone, a tablet device, a personal computer (PC) device, and so forth).

One or more components of the pulse oximeter systems 100 (e.g., the wearable device 102 and/or the monitor device 108) may include a controller providing a processor, a communications interface, and/or a memory. The processor provides processing functionality for the controller and may include any number of processors, micro-controllers, or other processing systems and resident or external memory for storing data and other information accessed or generated by the controller. The processor may execute one or more software programs which implement techniques described herein. The processor is not limited by the materials from which it is formed or the processing mechanisms employed therein, and as such, may be implemented via semiconductor(s) and/or transistors (e.g., using electronic Integrated Circuit (IC) components), and so forth.

A communications interface is operatively configured to communicate with components of the pulse oximeter systems. For example, the transmitter 106 of the wearable device 102 can be implemented as a communications interface configured to transmit a detected oxygen level and/or a detected heart rate of a user to the monitor device 108, while the receiver 110 of the monitor device 108 can be implemented as a communications interface configured to receive a detected oxygen level and/or a detected heart rate of a user from the wearable device 102. A communications interface is also communicatively coupled with a processor (e.g., for communicating inputs from the wearable device 102 to a processor of the monitor device 108).

The communications interface can also be configured to communicate with a variety of different networks, including but not necessarily limited to: the Internet, a cellular telephone network, a local area network (LAN), a wide area network (WAN), a wireless network (e.g., using a wireless sensor network technology, such as ANT), a public telephone network, an intranet, and so on. For example, a communications interface of the monitor device 108 can be configured to transmit a detected oxygen level of a user, a detected heart rate of a user, an alert, or the like to a mobile telephone device, such as a smart phone 120 and/or another monitor device, such as a portable, handheld monitoring unit 118. In some embodiments, the smart phone 120 is equipped with a receiver device 124 configured to receive wireless communications from the monitor device 108. Further, a communications interface of the wearable device 102 can be configured to transmit a detected oxygen level of a user, a detected heart rate of a user, an alert, or the like to a mobile telephone device, such as a smart phone 120, a pager, and so forth. For example, in some implementations, the monitor device 108 comprises a smart phone.

The memory is an example of tangible computer-readable media that provides storage functionality to store various data associated with operation of the controller, such as software programs and/or code segments, or other data to instruct a processor and possibly other components of the controller to perform the steps described herein. For example, the memory may be used to store one or more rule sets configured to allow a processor to provide an alert (e.g., one or more thresholds associated with an established oxygen level, an established heart rate, and so forth). In implementations, a wide variety of types and combinations of memory may be employed. The memory may be integral with the processor, may comprise stand-alone memory, or may be a combination of both.

The memory may include, but is not necessarily limited to: removable and non-removable memory components, such as Random Access Memory (RAM), Read-Only Memory (ROM), Flash memory (e.g., a Secure Digital (SD) memory card, a mini-SD memory card, a micro-SD memory card), magnetic memory, optical memory, Universal Serial Bus (USB) memory devices, and so forth. In embodiments, the memory may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system for monitoring an infant, comprising:
a first device configured to be wearable by an infant at the infant's foot, the wearable device comprising a sensor configured to detect an oxygen level of the infant and a heart rate of the infant, and a transmitter coupled with the sensor for transmitting an indication of the infant's detected oxygen level and the infant's detected heart rate;
a second device comprising a receiver for receiving the indication of the infant's detected oxygen level and the infant's detected heart rate from the first device,
a processor configured to establish an oxygen level and a heart rate for the infant by measuring values for both the oxygen level and the heart rate, the values staying substantially constant during a first period of time, the processor further configured for comparing the infant's detected oxygen level and the infant's detected heart rate to the established oxygen level and the established heart rate for the infant, the processor configured to compare the infant's detected oxygen level to a lower threshold being a decrease of the established oxygen level of five percent (5%) or more, the processor configured to compare the infant's detected heart rate to a lower threshold being a decrease of a percentage of the established heart rate and an upper threshold being an increase of a percentage of the established heart rate,
an identifier for providing an alert when the infant's detected oxygen level or the infant's detected heart rate is outside the thresholds for either oxygen level or heart rate, the identifier providing an alert when the oxygen level or the heart rate are not provided for a preprogrammed time period, and a second transmitter for transmitting at least one of the indication of the infant's detected oxygen level, the infant's detected heart rate, or the alert; and a mobile monitoring device for receiving the at least one of the indication of the infant's detected oxygen level, the infant's detected heart rate, or the alert from the second device and displaying the at least one of the indication of the infant's detected oxygen level, the infant's detected heart rate, or the alert.

2. The system as recited in claim 1, wherein the sensor comprises a pulse oximeter.

3. The system as recited in claim 1, wherein the second device comprises at least one of a base station monitor, a handheld monitor, or a smart phone monitor.

4. The system as recited in claim 1, wherein the sensor comprises a sensor configured to detect at least one of a presence or an absence of motion associated with the infant, and the transmitter is configured to transmit the at least one of the presence or the absence of motion associated with the infant.

5. The system as recited in claim 1, wherein the identifier is configured to provide an alert comprising at least one of an audible alarm, a visual alarm, a flashing display readout, an indicator light, a haptic feedback alarm, or an electronic message.

6. A method for monitoring an infant, comprising:
receiving, at a first monitoring device, an indication of an oxygen level of an infant and a heart rate of the infant, the infant's oxygen level and the infant's heart rate detected by a wearable device configured to be wearable by the infant at the infant's foot;
measuring values for both the oxygen level and the heart rate of the infant, the values staying substantially constant during a first period of time to establish an oxygen level and a heart rate for the infant by a processor;
comparing, by the processor, the infant's detected oxygen level and the infant's detected heart rate to the established oxygen level and the established heart rate for the infant, the processor configured to compare the infant's detected oxygen level to a lower threshold being a decrease of the established oxygen level of five percent (5%) or more, the processor configured to compare the infant's detected heart rate to a lower threshold being a decrease of a percentage of the established heart rate and an upper threshold being an increase of a percentage of the established heart rate;
providing an alert when the infant's detected oxygen level or the infant's detected heart rate is outside the thresholds for either oxygen level or heart rate, and providing an alert when the oxygen level or the heart rate are not provided for a preprogrammed time period;
transmitting, from the first monitoring device, at least one of the infant's detected oxygen level with the infant's detected heart rate or the alert;
receiving, at a mobile monitoring device, at least one of the infant's detected oxygen level with the infant's detected heart rate or the alert from the first monitoring device; and
displaying, at the mobile monitoring device, the at least one of the infant's detected oxygen level with the infant's detected heart rate or the alert.

7. The method as recited in claim 6, further comprising receiving an indication of at least one of a presence or an absence of motion associated with the infant, and providing the alert when the infant's detected heart rate is greater than the infant's upper threshold heart rate and the at least one of the presence or the absence of motion associated with the infant indicates an absence of motion associated with the infant.

8. The method as recited in claim 7, wherein the indication of at least one of the presence or the absence of motion associated with the infant is received from the wearable device.

9. The method as recited in claim 6, further comprising receiving at least one of an indication of a room temperature, a light level, a noise, or a vibration from the wearable device.

10. A system for monitoring an infant, comprising:
a wearable device comprising a pulse oximeter configured to detect an oxygen level of an infant at the infant's foot and a heart rate of the infant at the infant's foot, and a transmitter coupled with the pulse oximeter for transmitting an indication of the infant's detected oxygen level and the infant's detected heart rate;
a monitor comprising a receiver for receiving the indication of the infant's detected oxygen level and the infant's detected heart rate from the wearable device,
a processor configured to establish an oxygen level and a heart rate for the infant by measuring values for both the oxygen level and the heart rate, the values staying substantially constant during a first period of time, the processor further configured for comparing the infant's detected oxygen level and the infant's detected heart rate to the established oxygen level and the established heart rate for the infant, the processor configured to compare the infant's detected oxygen level to a lower threshold being a decrease of five percent (5%) or more of the established oxygen level, the processor configured to compare the infant's detected heart rate to a lower threshold being a decrease of a percentage of the established heart rate and an upper threshold being an increase of a percentage of the established heart rate;
an identifier for providing an alert when the infant's detected oxygen level or the infant's detected heart is outside the thresholds for either oxygen level or heart rate, the identifier providing an alert when the oxygen level or the heart rate are not provided for a preprogrammed time period; and a second transmitter for transmitting at least one of the indication of the infant's detected oxygen level, the infant's detected heart rate, or the alert; and
a mobile monitoring device for receiving the at least one of the indication of the infant's detected oxygen level, the infant's detected heart rate, or the alert from the monitor and displaying the at least one of the indication of the infant's detected oxygen level, the infant's detected heart rate, or the alert.

11. The system as recited in claim 10, wherein the monitor comprises at least one of a base station monitor, a handheld monitor, or a smart phone monitor.

12. The system as recited in claim 10, wherein the wearable device comprises a sensor configured to detect at least one of a presence or an absence of motion associated with the infant, and the transmitter is configured to transmit the at least one of the presence or the absence of motion associated with the infant.

13. The system as recited in claim 10, wherein the identifier is configured to provide an alert comprising at least one of an audible alarm, a visual alarm, a flashing display readout, an indicator light, a haptic feedback alarm, or an electronic message.

* * * * *